US011033607B2

(12) United States Patent
Husain et al.

(10) Patent No.: US 11,033,607 B2
(45) Date of Patent: Jun. 15, 2021

(54) PEPTIDES AND METHODS FOR PREVENTING ISCHEMIC TISSUE INJURY

(71) Applicant: University Health Network, Toronto (CA)

(72) Inventors: Mansoor Husain, Toronto (CA); Dhanwantee Mundil, Brampton (CA)

(73) Assignee: University Health Network, Toronto (CA)

( * ) Notice: Subject to any disclaimer, the term of this patent is extended or adjusted under 35 U.S.C. 154(b) by 350 days.

(21) Appl. No.: 14/438,375

(22) PCT Filed: Oct. 28, 2013

(86) PCT No.: PCT/CA2013/000920
§ 371 (c)(1),
(2) Date: Apr. 24, 2015

(87) PCT Pub. No.: WO2014/063239
PCT Pub. Date: May 1, 2014

(65) Prior Publication Data
US 2015/0246098 A1 Sep. 3, 2015

Related U.S. Application Data

(60) Provisional application No. 61/719,075, filed on Oct. 26, 2012.

(51) Int. Cl.
*A61K 38/26* (2006.01)

(52) U.S. Cl.
CPC .................................... *A61K 38/26* (2013.01)

(58) Field of Classification Search
None
See application file for complete search history.

(56) References Cited

U.S. PATENT DOCUMENTS

| | | | | |
|---|---|---|---|---|
| 7,833,531 B2 * | 11/2010 | O'Neil | ................... | A61K 38/26 424/178.1 |
| 2002/0147131 A1 * | 10/2002 | Coolidge | ............... | A61K 38/26 514/11.7 |
| 2006/0160740 A1 | 7/2006 | Efendic | | |
| 2011/0274747 A1 * | 11/2011 | Habener | .............. | C07K 14/605 424/450 |
| 2012/0053119 A1 * | 3/2012 | Habener | .............. | C07K 14/522 514/7.2 |

FOREIGN PATENT DOCUMENTS

| | | |
|---|---|---|
| CA | 2372947 | 11/2000 |
| WO | 2013006692 A2 | 1/2013 |
| WO | 2013022692 A1 | 2/2013 |

OTHER PUBLICATIONS

Tomas et al. (Trends Endocrinol Metab. Feb. 2010; 21(2):59-67).*
Geng et al., Hepatobiliary Pancreat Dis Int 2011; 10: 83-87.*
Husain et al., Cardio-Protective Peptide Therapy, May 11, 2017.*
World Heart Federation (downloaded on Jun. 19, 2017 from URL:< http://www.world-heart-federation.org/cardiovascular-health/cardiovascular-disease-risk-factors/diabetes/>).*
Walpole et al. (BMC Public Health 2012, 12:439).*
Torres-González et al. (Nephroprotective Effect of Sonchus oleraceus Extract against Kidney Injury Induced by Ischemia-Reperfusion in Wistar Rats) (Year: 2017).*
Bruno et al. (Current Treatment Options in Neurology (2010) 12:492-503) (Year: 2010).*
Reinbolt et al. (Support Care Cancer. May 2016; 24(5): 2173-2180) (Year: 2016).*
Dyck et al. (J Mol Cell Cardiol 34, 1099-1109 (2002)) (Year: 2002).*
Bao, W., et al., "Albiglutide, a Long Lasting Glucagon-Like Peptide-1 Analog, Protects the Rat Heart Against Ischemia/Reperfusion Injury: Evidence for Improving Cardiac Metabolic Efficiency." PloS ONE, Aug. 2011, vol. 6(8): e23570. doi:10.1371/journal.pone.0023570.
Mundil, D., et al., "GLP-1(28-36) Exerts Direct Cardioprotective Effects, Activating Pro-Survival Kinases and Soluable Adenylyl Cyclase." Circulation, Nov. 20, 2012, vol. 126(21) Suppl, Abstract 13657. (A).
Sharma, R., et al., "In Vitro Metabolism of the Glucagon-Like Peptide-1 (GLP-1)-Derived Metabolites GLP-1(9-36) amide and GLP-1(28-36)amide in Mouse and Human Hepatocytes." Drud Metab Dispos, Dec. 2013 (epub Sep. 20, 2013), vol. 41(12), pp. 2148-2157,.
Mundil, D., et al., "GLP-1 Receptor Agonists: A Clinical Perspective on Cardiovascular Effects." Diabetes & Vascular Disease Research, Apr. 2012, vol. 9(2), pp. 95-108. (B).
Ussher, J., et al., "Cardiovascular Biology of the Incretin System." Endocrine Reviews, Apr. 2012, 33(2), pp. 187-215.
Ban, K., et al., "Cardioprotective and vasodilatory actions of glucagon-like peptide 1 receptor are mediated through both glucagon-like peptide 1 receptor-dependent and -independent pathways." Circulation, 2008, 117, pp. 2340-2350.
Ban, K., et al., "Glucagon-like peptide (GLP)-1(9-36)amide-mediated cytoprotection is blocked by exendin(9-39) yet does not require the known GLP-1 receptor." Endocrinology, Apr. 2010, 151(4), pp. 1520-1531.
Buse, J.B., et al., "LEAD-6 Study Group Liraglutide once a day versus exenatide twice a day for type 2 diabetes: a 26-week randomised, parallel-group, multinational, open-label trial (LEAD-6)." Lancet, 2009, vol. 374(9683), pp. 39-47.

(Continued)

*Primary Examiner* — Sergio Coffa
(74) *Attorney, Agent, or Firm* — Bereskin & Parr LLP /S.E.N.C.R.L., s.r.l.; Laurence MacPhie

(57) ABSTRACT

Provided are GLP-1 C-terminal peptides and methods of use for the treatment or prevention of ischemic tissue injury. The peptides correspond to GLP-1(28-36). FIAWLVKGR and GLP-1(28-37) FIAWLVKGRG and are useful in the treatment or prevention of ischemic tissue injury, including ischemic heart disease or stroke.

19 Claims, 10 Drawing Sheets

Specification includes a Sequence Listing.

(56) References Cited

OTHER PUBLICATIONS

Diamant, M., et al., "Once weekly exenatide compared with insulin glargine titrated to target in patients with type 2 diabetes (DURATION-3): an open-label randomised trial." Lancet, 2010, vol. 375(9733), pp. 2234-2243.
Griffioen, K.J., et al., "GLP-1 receptor stimulation depresses heart rate variability and inhibits neurotransmission to cardiac vagal neurons." Cardiovasc Res, 2011, 89, pp. 72-78.
Ma, T., et al., "Glucagon-like peptide-1 cleavage product GLP-1(9-36) amide rescues synaptic plasticity and memory deficits in Alzheimer's disease model mice." Journal of Neuroscience, 2012, 32(40), pp. 13701-13708.
Noyan-Ashraf, M.H., et al., "GLP-1r agonist liraglutide activates cytoprotective pathways and improves outcomes after experimental myocardial infarction in mice." Diabetes, 2009, vol. 58, pp. 975-983.
Ohta, K., et al., "Elafin-overexpressing mice have improved cardiac function after myocardial infarction." American Journal of Physiology. Heart and Circulatory Physiology, 2004, vol. 287, pp. H286-292.
Parlevliet, E.T., et al., "Glp-1 treatment reduces endogenous insulin resistance via activation of central glp-1 receptors in mice fed a high-fat diet." American Journal of Physiology, Endocrinology and Metabolism, 2010, vol. 299, pp. E318-324.
Perry, T., et al., "Evidence of glp-1-mediated neuroprotection in an animal model of pyridoxine-induced peripheral sensory neuropathy." Experimental Neurology, 2007, 203, pp. 293-301.
Read, P.A., et al., "A pilot study to assess whether glucagon-like peptide-1 protects the heart from ischemic dysfunction and attenuates stunning after coronary balloon occlusion in humans." Circulation, Cardiovascular Interventions, 2011, 4, pp. 266-272.
Tomas, E., et al., "GLP-1-derived nonapeptide GLP-1(28-36)amide targets to mitochondria and suppresses glucose production and oxidative stress in isolated mouse hepatocytes." Regulatory Peptides, Apr. 11, 2011, 167(2-3), pp. 177-184. (A).
Zhang, J., et al., "Continuous stimulation of human glucagon-like peptide-1 (7-36) amide in a mouse model (nod) delays onset of autoimmune type 1 diabetes." Diabetologia, 2007, 50, pp. 1900-1909.
Liu, Z., et al., "GLP1-derived nonapeptide GLP1(28-36)amide protects pancreatic β-cells from glucolipotoxicity." Journal of Endocrinology, May 1, 2012, 213, pp. 143-154.
Orskov, C., et al., "Biological effects and metabolic rates of glucagon-like peptide-1 7-36 amide and glucagonlike peptide-1 7-37 in healthy subjects are indistinguishable." Diabetes, May 1993, vol. 42(5), pp. 658-661.
International Search Report (completed on Dec. 20, 2013) and Written Opinion (completed Jan. 27, 2014) for corresponding PCT Application No. PCT/CA2013/000920.
Burgmaier, M., et al., "Glucagon-like peptide-1 (GLP-1) and its split products GLP-1(9-37) and GLP-1(28-37) stabilize atherosclerotic lesions in apoe-/-mice." Atherosclerosis, 2013, vol. 231, pp. 427-435.
Tomas, E., et al., "GLP-1-derived nanapeptide GLP-1(28-36)amide inhibits weight gain and attenuates diabetes and hepatic steatosis in diet-induced obese mice." Regulatory Peptides, 2011, vol. 169, No. 1, pp. 43-48. (B).

* cited by examiner

A

B

A

B

PEPTIDES AND METHODS FOR PREVENTING ISCHEMIC TISSUE INJURY

CROSS REFERENCE TO RELATED APPLICATIONS

This application is a national phase entry of PCT/CA2013/000920 filed Oct. 28, 2013 (which designates the U.S.) which claims priority to U.S. Provisional Patent Application No. 61/719,075 filed Oct. 26, 2012, the contents of which are incorporated by reference herein in their entirety.

INCORPORATION OF SEQUENCE LISTING

A computer readable form of the Sequence Listing "10723-P42864US01_SequenceListing.txt" (4,096 bytes), submitted via EFS-WEB and amended on Dec. 29, 2015, is herein incorporated by reference.

FIELD OF THE INVENTION

The present invention provides peptides useful as agents for preventing ischemic tissue injury and more specifically peptides corresponding to all or part of the C-terminal domain of GLP-1 and associated methods for the treatment or prevention of ischemic tissue injury.

BACKGROUND OF THE INVENTION

Endogenous Glucagon-like peptide-1 (80%: GLP-1 $(7-36)^{amide}$, a.k.a. GLP-1; and 20%: GLP-1$(7-37)^{amide}$) is an incretin hormone that regulates glucose homeostasis and is rapidly degraded by dipeptidyl peptidase-4 (DPP4) to GLP-1$(9-36)^{amide}$ (and to GLP-1$(9-37)^{amide}$.) Both GLP-1 and GLP-1$(9-36)^{amide}$ are known to be cardioprotective against ischemia/reperfusion (I/R) injury in wild-type and GLP-1 receptor knockout mice. GLP-1 and GLP-1(9-36 amide) (as well as GLP-1$(7-37)^{amide}$ and GLP-1$(9-37)^{amide}$) are believed to be cleaved by neutral endopeptidase 24.11 to release the C-terminal fragment nonapeptide GLP-1$(28-36)^{amide}$ (and GLP-1$(28-37)^{amide}$ respectively).

While GLP-1 and GLP-1$(9-36)^{amide}$ are known to be cardioprotective, little is known about the effects of the C-terminal fragment nonapeptide GLP-1$(28-36)^{amide}$ outside of its glucoregulatory effects.

There is a need for new agents and associated methods for treating or preventing ischemic tissue injury.

SUMMARY OF THE INVENTION

The present disclosure provides peptides that are useful as agents for the protection of ischemic tissue injury. In one embodiment, the peptides are useful as cardioprotective agents. In another embodiment, the peptides are useful as neuroprotective agents. The peptides correspond to fragments of the C-terminal domain of Glucagon-like peptide-1 (GLP-1), or peptides that have sequence identity to fragments of the C-terminal domain of GLP-1. In one embodiment, the peptide comprises, consists essentially of, or consists of the nonapeptide GLP-1(28-36) or the decapeptide GLP-1(28-37). In one embodiment, the C-terminus of the peptides described herein is amidated. In one embodiment, the peptide comprises, consists essentially of, or consists of the amino acid sequence FIAWLVKGR (SEQ ID NO: 1) or FIAWLVKGRG (SEQ ID NO: 2), optionally wherein the C-terminus of the peptide is amidated.

It has surprisingly been determined that the GLP-1$(28-36)^{amide}$ peptide protects tissue from injury under conditions of ischemic stress. Pre-treatment with GLP-1$(28-36)^{amide}$ was shown to reduce infarct size and improve functional recovery measured by Left Ventricle Developed Pressure (LVDP) in a mouse model of ischemia/reperfusion injury. Infarct size and LVDP recovery post-reperfusion were significantly improved in mice pretreated with GLP-1$(28-36)^{amide}$ compared to a saline control or scrambled peptide. Improvements in infarct size and LVDP recovery were comparable to mice treated with the longer peptides GLP-1$(7-36)^{amide}$ and GLP-1 $(9-36)^{amide}$ Furthermore, pretreatment with GLP-1$(28-36)^{amide}$ curtailed the release of the cell death marker lactate dehydrogenase (LDH) relative to untreated controls and at similar levels to mice treated with the longer peptide GLP-1$(7-36)^{amide}$ following ischemia/reperfusion injury.

The inventors have demonstrated that the protective effects of the GLP-1$(28-36)^{amide}$ peptide are blocked by the soluble adenylate cyclase inhibitor KH7, but not by the transmembrane adenylate cyclase inhibitor 2,5 dideoxyadenosine. The GLP-1$(28-36)^{amide}$ peptide was also shown to cause a dose-dependent increase in intracellular cAMP levels in vitro using cultured human coronary smooth muscle cells (hCSMCs). Release of cAMP by the GLP-1$(28-36)^{amide}$ peptide was shown to be dependent on soluble adenylate cyclase in vitro using hCSMCs but not on transmembrane adenylate cyclase.

The smaller protective peptides described herein that comprise, consist essentially of, or consist of all or part of the amino acid sequence FIAWLVKGR (SEQ ID NO: 1) or FIAWLVKGRG (SEQ ID NO: 2) exhibit a number of advantages over longer GLP-1 derived peptides such as GLP-1(7-36) or GLP-1(9-36). For example, smaller peptides are generally easier to synthesize and have better pharmacokinetic properties. Furthermore, while the longer GLP-1(7-36) and GLP-1(9-36) peptides are known to bind to and activate the GLP-1 Receptor (GLP1R), the smaller peptides described herein do not activate GLP1R or activate transmembrane adenylate cyclase. Remarkably, as shown in Examples 1-3, the cardioprotective effects of the peptides described herein such as GLP-1$(28-36)^{amide}$ occur independently of the GLP1 receptor through a soluble adenylate cyclase (sAC) dependent mechanism. A schematic showing the proposed mechanism for the sAC-dependent action of the peptides such as GLP-1$(28-36)^{amide}$ is shown in FIG. 8B. Activation of GLP1R by the GLP-1(7-36) and GLP-1(9-36) peptides is associated with a number of potentially undesirable side effects in vivo, such as vasodilation (see Ban et al. 2008) and in the case of GLP-1 and known GLP-1 receptor agonists (GLP-1RA) such as liraglutide and exenatide an increase in heart rate (see Diamant et al. 2010; Buse et al. 2009 and Griffioen et al. 2011).

Accordingly, in one aspect of the disclosure there is provided an isolated peptide corresponding to all or part of the C-terminal domain of GLP-1. In one embodiment, the peptide corresponds to all or part of GLP-1(28-36) or GLP1(28-37). In one embodiment, the C-terminus of the polypeptide is amidated. Optionally, the peptide comprises all or part of the amino acid sequence FIAWLVKGR (SEQ ID NO: 1) or FIAWLVKGRG (SEQ ID NO: 2). In one embodiment, the peptide comprises at least 5, 6, 7, 8 or 9 consecutive amino acids of the amino acid sequence FIAWLVKGR or FIAWLVKGRG. Optionally, the peptide consists of 5, 6, 7, 8 or 9 consecutive amino acids of the amino acid sequence FIAWLVKGR (SEQ ID NO: 1) or FIAWLVKGRG (SEQ ID NO: 2). In one embodiment, the peptide consists of the amino acid sequence FIAWLVKGR (SEQ ID NO: 1) or FIAWLVKGRG (SEQ ID NO: 2). In one embodiment, the peptide increases the intracellular level of cAMP.

In one embodiment, the peptides described herein are protective against ischemic tissue injury. For example, in one embodiment, the peptides described herein are protective against neural injury following stroke. In one embodiment, the peptides described herein are protective against myocardial tissue injury following a myocardial ischemic event. In one embodiment, the peptides are cardioprotective against ischemia/reperfusion injury. In one embodiment, the peptide is cardioprotective against myocardial infarction and/or ischemia-induced cell death. In one embodiment, the peptides are protective against the loss of heart function following an ischemic event. For example, in one embodiment the peptides are cardioprotective against ischemia-induced loss of left ventricular developed pressure (LVDP). The peptides described have been determined to increase the levels of intracellular cAMP in cardiac smooth muscle cells. In one embodiment, the increase in intracellular cAMP is dependent on soluble adenylate cyclase and not dependent on transmembrane adenylate cyclase.

In another aspect the present disclosure provides pharmaceutical compositions comprising a peptide protective against tissue injury as described herein and one or more pharmaceutically acceptable carriers.

The peptides described herein are useful for the treatment or prevention of tissue damage following an ischemic event. Accordingly, in one embodiment, there is provided a method for the treatment or prevention of ischemic tissue injury comprising administering to a subject in need thereof a peptide or pharmaceutical composition as described herein. Also provided in the use of a peptide as described herein for the treatment or prevention of ischemic tissue injury in a subject in need thereof. Also provided is a peptide as described herein for use in the treatment of ischemic tissue injury in a subject in need thereof. In one embodiment, the peptide comprises, consists essentially of, or consists of, all or part of GLP-1(28-36) or GLP-1(28-37). In one embodiment, the peptide comprises, consists essentially of, or consists of, all or part of the amino acid sequence FIAWLVKGR (SEQ ID NO: 1) or FIAWLVKGRG (SEQ ID NO: 2). Optionally, the peptides are amidated at the C-terminus.

The methods and uses described herein are particularly useful for treating or preventing ischemic tissue damage in subjects at risk of an ischemic event. In one embodiment, the methods and uses described herein are useful for treating or preventing ischemic tissue damage in a subject at risk of stroke or ischemic heart disease. In one embodiment, the subject has an increased risk of ischemic heart disease or cardiovascular disease relative to a normal population. For example, in one embodiment, the subject has previously had a myocardial infarction or stroke. In some embodiments, the subject has an increased risk of diabetes or cardiotoxicity due to the subject taking medication with known cardiotoxic effects. In one embodiment, the methods described herein involve the use or administration of a protective peptide or composition as a prophylactic for the prevention of tissue damage following an ischemic event. Optionally the methods and uses described herein involve the administration or use of a protective peptide or composition after an ischemic event has been detected in a subject. In some embodiments the peptide or composition may be used, formulated for use, or administered to the subject on a regular dosing schedule, such as about every day, every 2 days, every 3 days every 4 days, every 5 days, every 6 days, or every week. In some embodiments the peptide or composition may be used, formulated for use or administered to the subject on a regular dosing schedule such as every 10 days, every 2 weeks, every 3 weeks or every month etc.

In one embodiment, the methods described herein involve the use, formulation for use or administration to the subject a dose of the protective peptide an amount sufficient to result in a steady state plasma concentration of about 1 picomolar to about 10 nanomolar. Optionally, the methods and uses described herein involve the use, formulation for use or administration to the subject a dose of the protective peptide in an amount sufficient to result in a steady state plasma concentration greater than about 10 nanomolar. Optionally, the methods and uses described herein involve the use, formulation for use or administration to the subject a dose of the protective peptide in an amount sufficient to result in a steady state plasma concentration between about 50 picomolar and 10 nanomolar, or between about 100 picomolar and 5 nanomolar.

Also provided is in the use of a peptide as described herein in the manufacture of a medicament or pharmaceutical composition for the treatment or prevention of ischemic tissue injury.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the invention will be described in relation to the drawings in which.

(7-36)amide (0.3 nmol/L; n=13; 67.3±8.6%), GLP-1 (9-36)$^{amide}$ (0.3 nmol/L; n=8; 64.3±9.6%), GLP-1 (28-36)$^{amide}$ (6 nmol/L; n=12; 57.6±6.6%), SCRAM (28-36)$^{amide}$ (6 nmol/L; n=4; 35.9±5.6%). All data are mean±SE. *P<0.05 vs untreated control by one-way ANOVA.

Figure 4:
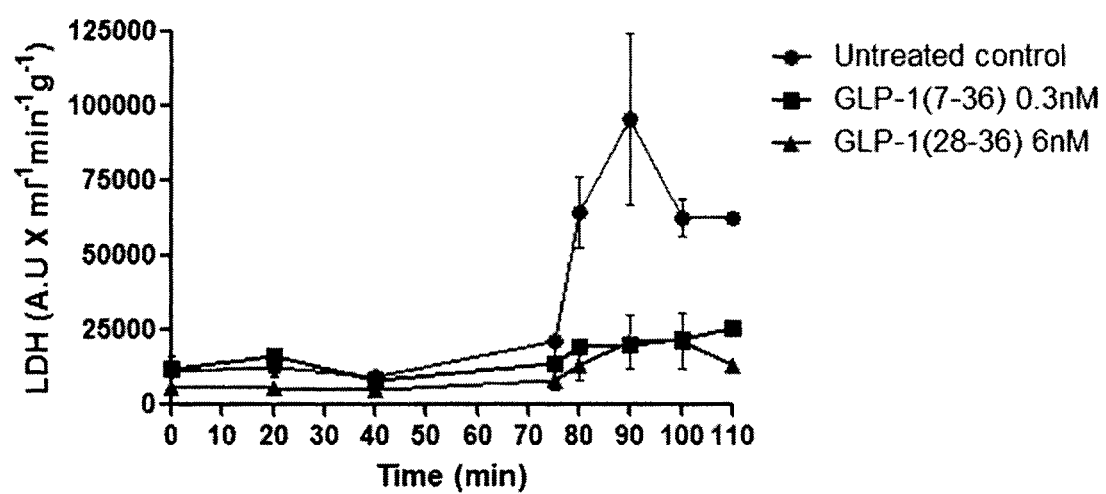

FIG. 4 shows LDH release in coronary effluents of isolated perfused hearts of WT mice undergoing I/R injury. Effect of no treatment (control; n=3), GLP-1(28-36) (6 nmol/L; n=4), GLP-1(7-36)$^{amide}$ (0.3 nmol/L; n=5) pretreatments at specific timepoints of I/R protocol. All data are mean±SE. *P<0.05 vs. untreated control by 1-way ANOVA at time point 110 min.

Figure 5:
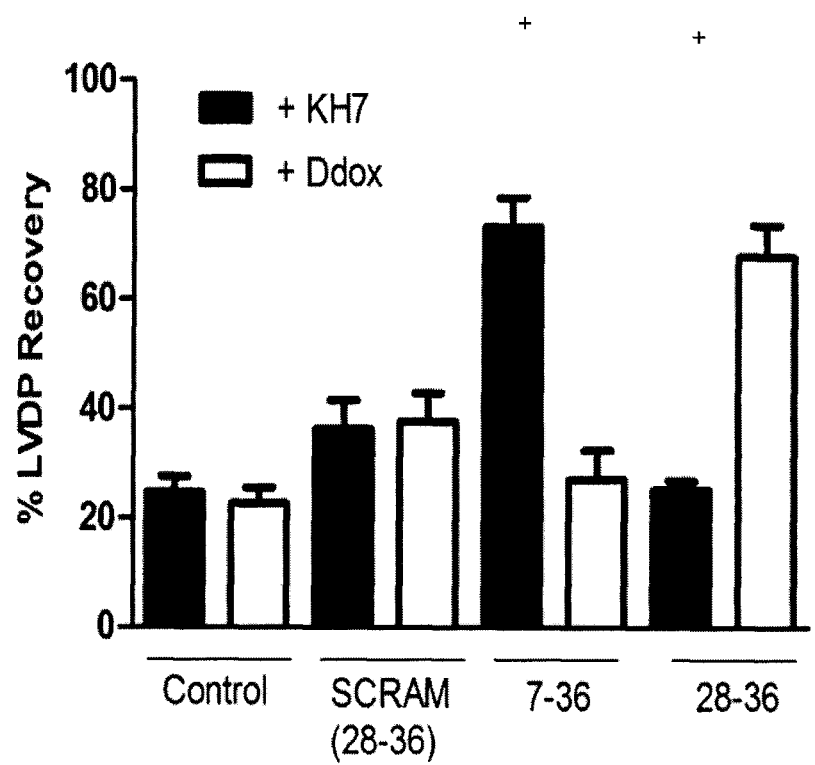

FIG. 5 shows that functional recovery after I/R injury in WT mice pretreated with GLP-1(28-36)$^{amide}$ is blocked by soluble adenylate cyclase (AC) inhibitor, KH7 (2.4 uM), but not transmembrane AC inhibitor, 2,5 dideoxyadenosine (12 uM). n=3-5 for each treatment conditions. All data are mean±SE. *P<0.05 vs untreated control by one-way ANOVA.

Figure 6:
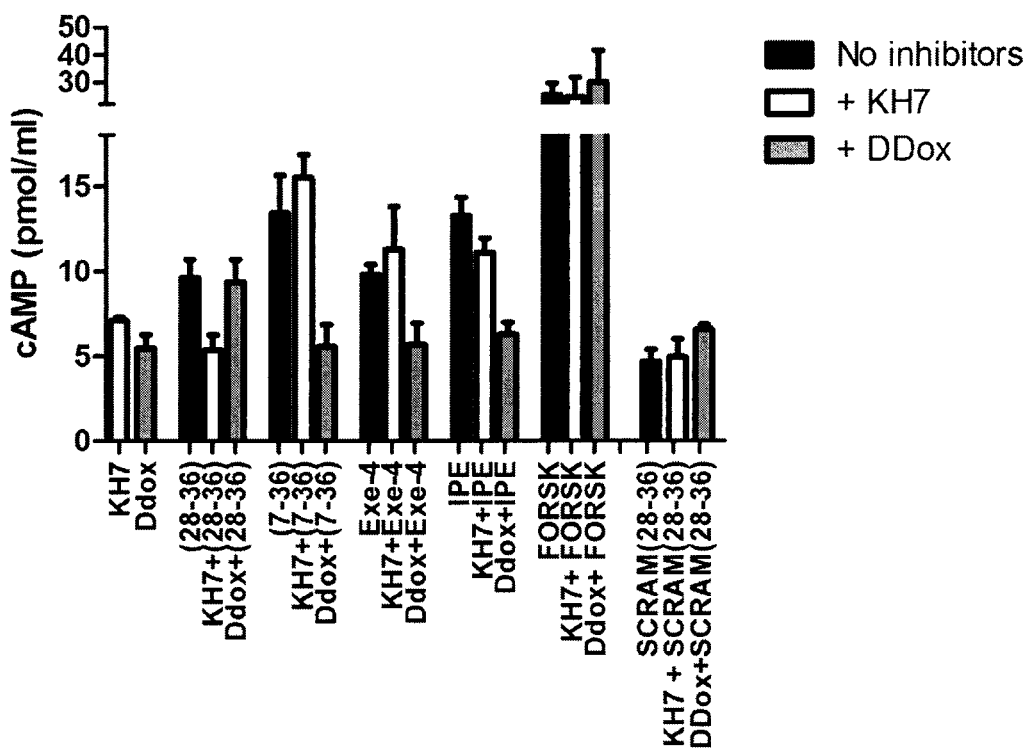

FIG. 6 shows that GLP-1(28-36)$^{amide}$ mediated cAMP release in cultured human coronary smooth muscle cells is dependent on soluble adenylate cyclase but is not dependent on transmembrane adenylate cyclase. GLP-1, Exe-4, IPE and Forskolin doses: 3 uM; KH7 dose is 25 uM. (Ddox) dose is 25 uM. Data represent mean±SE (n=3). *P<0.05 by one-way ANOVA.

Figure 7:
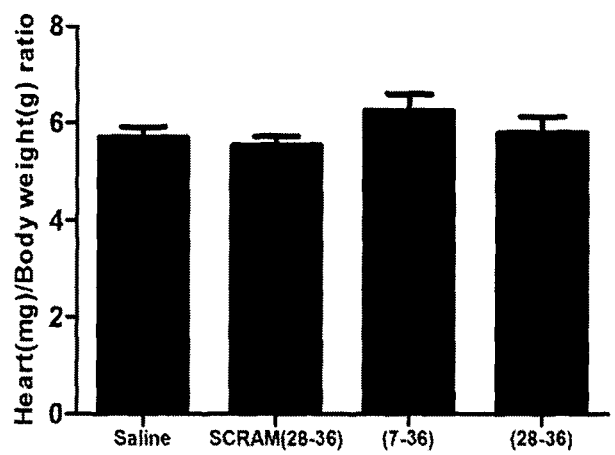
Figure 7:
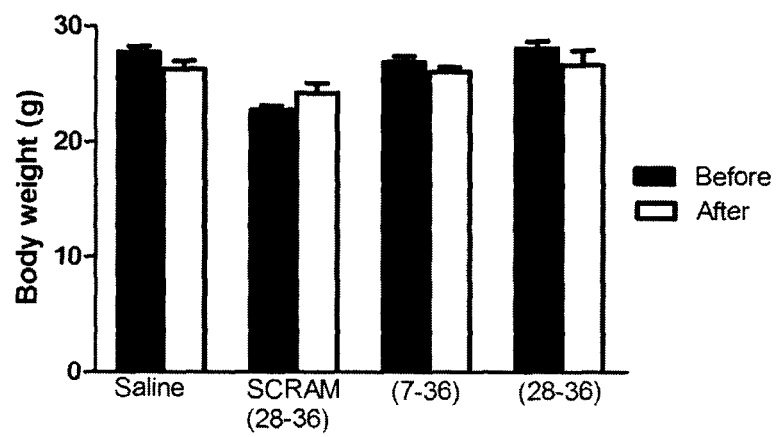
Figure 7:
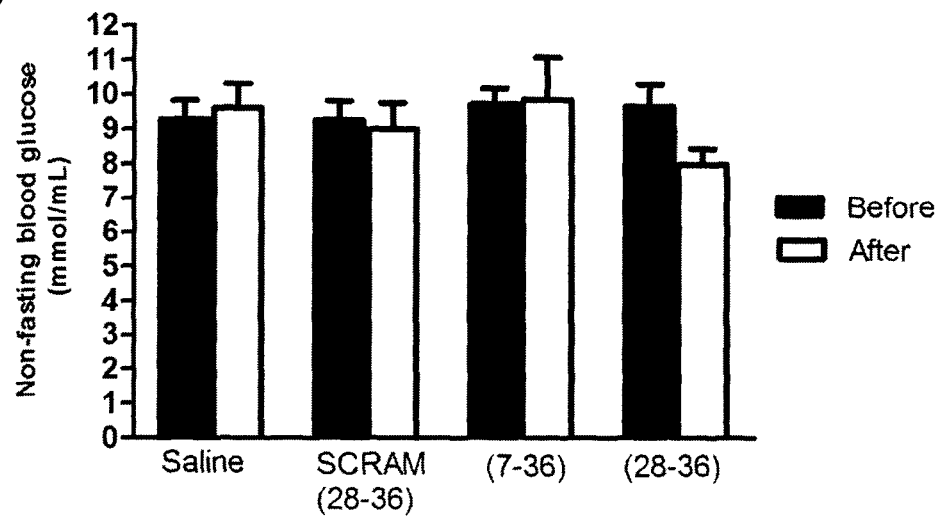

FIG. 7 shows the effects of treatment with GLP-1 peptides on heart weight, body weight and non-fasting blood glucose levels. FIG. 7A shows no changes in heart/body weight ratios amongst the treatment groups. FIG. 7B shows non-significant changes in body weight. FIG. 7C shows non-significant changes in non-fasting blood glucose levels before and after drug treatment for each group. All data are mean±SE. *P<0.05 vs saline and Scram control by one-way ANOVA.

Figure 8:
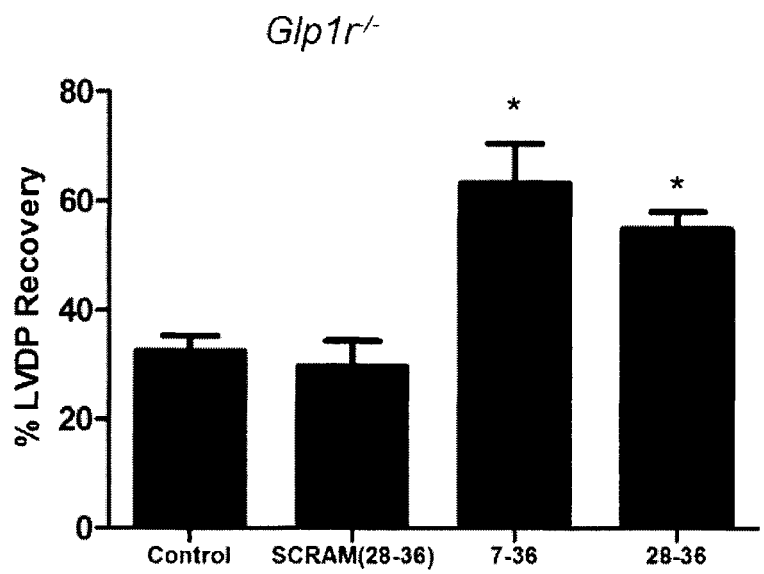
Figure 8:
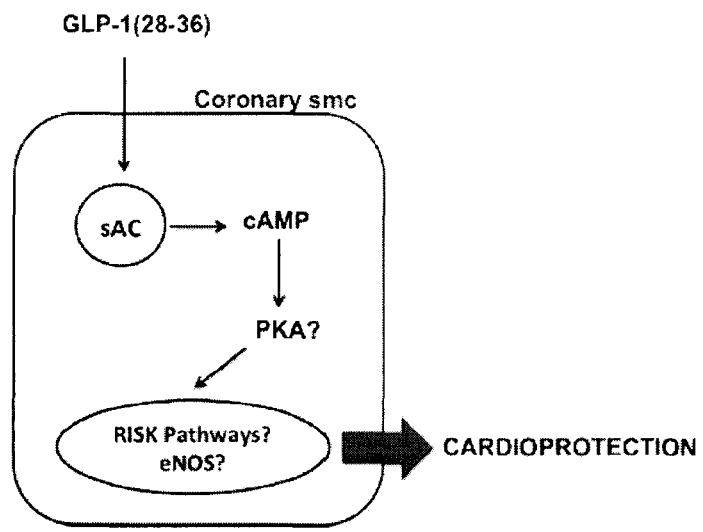

FIG. 8A shows the effect of no treatment (control), and pretreatments with GLP-1(7-36) (0.3 nM), GLP-1(28-36) (6 nM), and SCRAM(28-36) (6 nM) on LVDP recovery in Glp1r−/− (n=3-5/group) mice. FIG. 8B shows a schematic of the proposed mechanism for sAC-dependent action of GLP-1(28-36) in cardioprotection in vascular cells.

Figure 9:
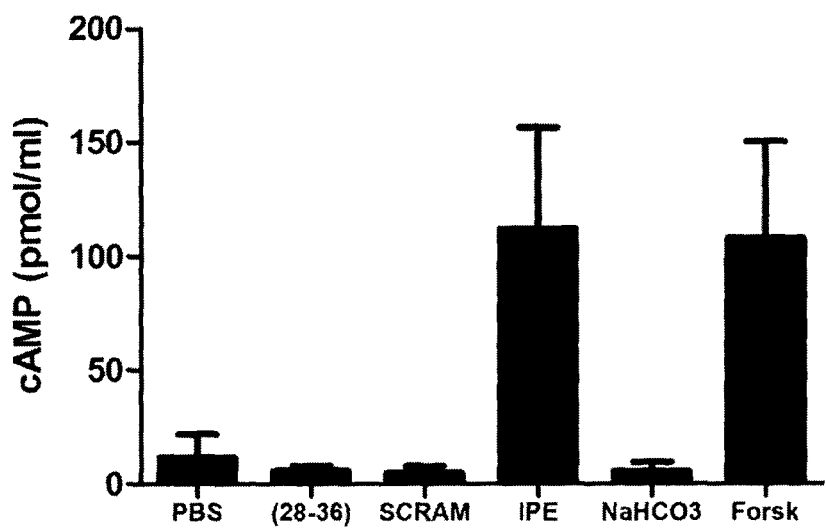
Figure 9:
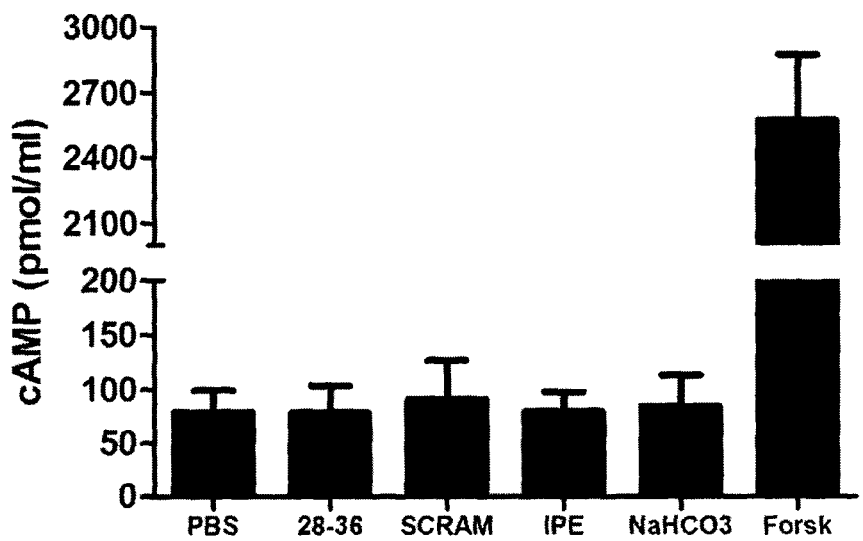

FIG. 9 shows that GLP-1(28-36)$^{amide}$ does not stimulate cAMP release from cardiac myocytes. Neonatal mouse ventricular myocytes (FIG. 9A) and atrial HL-1 myocyte cell lines (FIG. 9B) were pretreated with 250 uM IBMX for 30 min followed by treatment with GLP-1(28-36) and SCRAM(28-36) (30 nM each) or IPE and Forsk (10 uM each) or bicarbonate (25 mM) for 10 min. Cells were then lysed for measurement of cytoplasmic cAMP levels. Data represent mean±SE (n=3; triplicate wells for each replicate).

Figure 10:
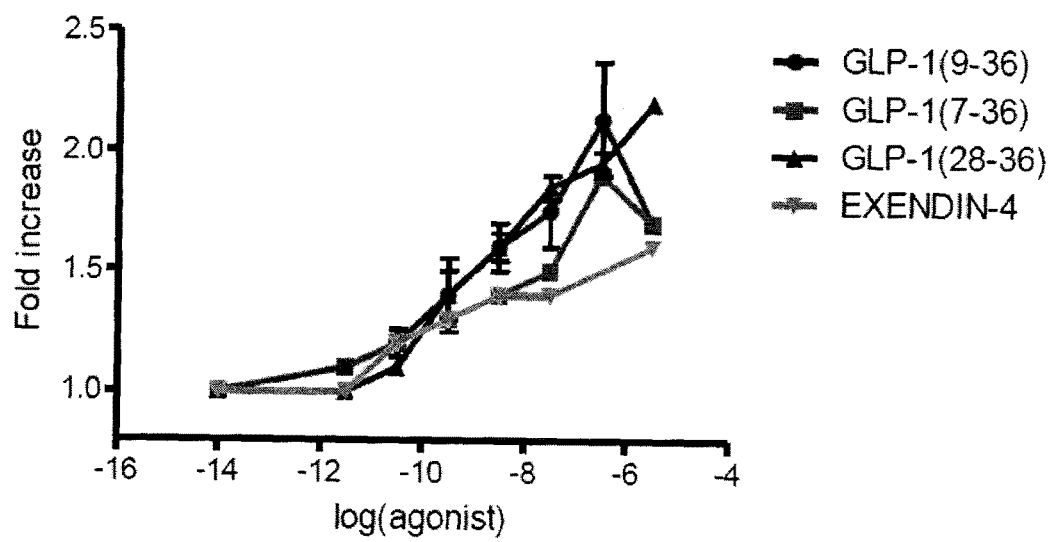

FIG. 10 shows that GLP-1 peptides including GLP-1(28-36) caused a dose-dependent increase in cAMP from hCSMCs.

Figure 11:
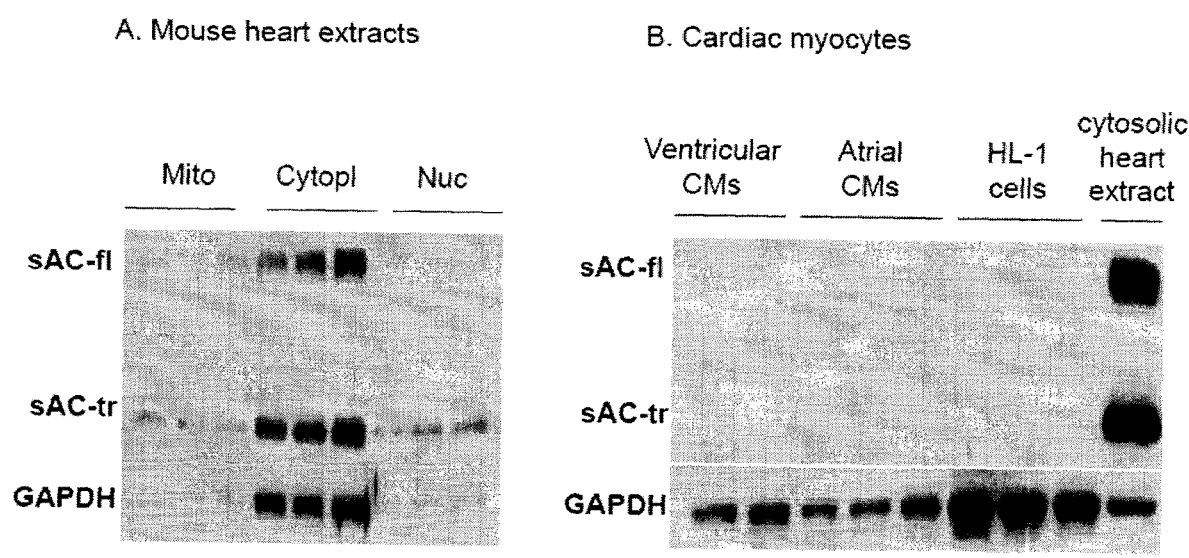

FIG. 11 shows that soluble adenylyl cyclase protein is expressed in heart tissues but not cardiac myocytes. FIG. 12A: mouse heart cellular lysates (mitochondrial, cytoplasmic and nuclear) were prepared by differential centrifugation. FIG. 12B: whole cell lysates were prepared from HL-1 cells and primary cultured neonatal mouse ventricular and atrial cardiac myocytes. Western blotting was performed against monoclonal sAC antibody with GAPDH as loading control. sACfl full length sAC 180KD); sAC-tr (truncated sAC 50KD).

DETAILED DESCRIPTION OF THE INVENTION

Definitions

As used herein, "protective" refers to the effect of an agent that helps to prevent tissue injury following an ischemic event. As used herein, "tissue injury" optionally includes organ damage or a reduction or loss in organ function following an ischemic event.

As used herein "ischemic event" refers to any temporary or continuous blockage or restriction in blood flow to an organ or tissue causing a shortage of oxygen and/or glucose in the organ or tissue. Examples of an ischemic event include, but are not limited to, atherosclerosis, thrombosis or embolism which e.g. results in a reduced blood supply to an organ such as the brain or heart or other vital organ. Optionally, the term "ischemic event" includes a myocardial infarction, heart attack or stroke.

As used herein, "ischemic tissue injury" refers to a condition characterized by ischemia (reduced blood supply) to a tissue or organ. Ischemic tissue injury may be the result of an ischemic event, coronary artery disease (atherosclerosis of the coronary arteries), hypertension, hypercholesterolemia, diabetes, stroke or any other condition that results in reduction of blood flow to a tissue or organ. In one event, the ischemic tissue injury is a result of ischemic heart disease.

As used herein, "treatment or prevention of ischemic tissue injury" refers to protecting tissue from acute or chronic exposure to ischemic events. For example, "treating or preventing ischemic heart disease" optionally includes the prophylactic treatment of a subject in order to reduce injury caused by an ischemic event. In one embodiment, the methods and uses described herein are useful for treating or preventing ischemic heart disease or myocardial ischemia.

As used herein, "subject" refers to any member of the animal kingdom, such as a mammal. In one embodiment the subject is a human.

As used herein, "cardiotoxicity" refers to the occurrence of heart electrophysiology dysfunction or/and muscle damage. In some embodiments cardiotoxicity results in the heart becoming weaker and not as efficient in pumping and therefore circulating blood.

Peptides of the Invention

The present disclosure provides peptides that are useful as cardioprotective agents. In an embodiment, the peptides have a sequence that corresponds to all or part of the C-terminal domain of GLP-1. In one embodiment, the peptide corresponds to all or part of GLP-1(28-36) or GLP-1(28-37). For example, in one embodiment the peptides described herein include all or part of the amino acid sequence FIAWLVKGR (SEQ ID NO: 1) or FIAWLVKGRG (SEQ ID NO: 2). Optionally, the peptides consist of 5, 6, 7, 8 or 9 amino acids of the amino acid sequence FIAWLVKGR (SEQ ID NO: 1) or FIAWLVKGRG (SEQ ID NO: 2).

Optionally, the peptides described herein are amidated at the C-terminus. A peptide that is amidated at the C-terminus does not terminate with a carboxylic acid group, but rather with an amide group such as $CONH_2$. For example, as used herein the terms "GLP-1(28-36)$^{amide}$" and "GLP-1(28-36)-$NH_2$" refer to the same amidated polypeptide. In one embodiment, the peptides described herein include polypeptides amidated at the C-terminus that comprise, consist essentially of, or consist of all or part of the amino acid sequence FIAWLVKGR (SEQ ID NO: 1).

In one embodiment, the peptides described herein share sequence identity with all or part of the amino acid sequence FIAWLVKGR (SEQ ID NO: 1) or FIAWLVKGRG (SEQ ID NO: 2). For example, in one embodiment the peptides described herein have at least 60%, 70%, 80% or 90% sequence identity with all or part of the amino acid sequence FIAWLVKGR (SEQ ID NO: 1) or FIAWLVKGRG (SEQ ID NO: 2).

Sequence identity is typically assessed by the BLAST version 2.1 program advanced search (parameters as above; Altschul, S. F., Gish, W., Miller, W., Myers, E. W. & Lipman, D. J. (1990) "Basic local alignment search tool." J. Mol. Biol. 215:403-410). BLAST is a series of programs that are available online through the U.S. National Center for Biotechnology Information (National Library of Medicine Building 38A Bethesda, Md. 20894) The advanced Blast search is set to default parameters. References for the Blast Programs include: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); Zhang, J. & Madden, T. L. (1997) "PowerBLAST: A new network BLAST application for interactive or automated sequence analysis and annotation." Genome Res. 7:649-656).

Optionally, the peptides described herein may be conjugated to another peptide or biomolecule in order to improve the pharmacokinetic or therapeutic qualities or the peptide. For example, in one embodiment the peptide is conjugated to a biologically compatible polymer such as polyethylene glycol (PEG) polymer. In an embodiment the peptides described herein optionally comprise a cell-penetrating peptide. For example, in an embodiment, there is provided a fusion protein comprising a peptide that and a cell-penetrating peptide. In an embodiment, the cell-penetrating peptide is a trans-activating transcriptional activator (TAT) peptide from Human Immunodeficiency Virus 1 (HIV-1). In an embodiment, the peptides described herein include cell-penetrating peptides such as myristoylated peptides. Optionally, the cell-penetrating peptide and the protective peptide are attached through a linker, such as another polypeptide sequence.

In one embodiment, the protective peptides described herein optionally include analogs of the aforementioned peptides. Analogs of the protein of the invention optionally include, but are not limited to an amino acid sequence containing one or more amino acid substitutions, insertions, deletions and/or mutations. Amino acid substitutions may be of a conserved or non-conserved nature. Conserved amino acid substitutions involve replacing one or more amino acids of the peptides of the invention with amino acids of similar charge, size, and/or hydrophobicity characteristics. When only conserved substitutions are made, the resulting analog should be functionally equivalent. Non-conserved substitutions involve replacing one or more amino acids of the amino acid sequence with one or more amino acids that possess dissimilar charge, size, and/or hydrophobicity characteristics. The analog is optionally a peptoid, which is an N-substituted polyglycine with amino acid R groups attached at the N atom. Another analog is optionally a peptide synthesized from D-amino acids rather than the natural L-amino acids.

The peptides of the invention are readily prepared by chemical synthesis using techniques well known in the art related to the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart). Other methods known in the art, such as recombinant technologies including but not limited to those disclose in disclosed by Sambrook et al (Sambrook J et al. 2000. Molecular Cloning: A Laboratory Manual (Third Edition), Cold Spring Harbor Laboratory Press), are also suitable for preparing the peptides described herein.

The isolated peptides described herein are useful for a number of purposes. In an embodiment, the peptides are useful as protective agents against ischemic tissue injury. In an embodiment, the peptides are useful for increasing the levels of cAMP in cardiac smooth muscle cells and other cell types, such as cardiac myocytes and neurons, etc.

Pharmaceutical Compositions

In an embodiment, there is provided a pharmaceutical composition comprising a protective peptide as described herein and a pharmaceutically acceptable carrier. The cardioprotective peptides of the invention are optionally formulated into a pharmaceutical composition for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. One aspect of the disclosure also includes the use of the cardioprotective peptides of the invention for preparation of a medicament for the treatment or prevention of ischemic heart disease.

In an embodiment, a peptide of the invention is combined with other components such as a carrier in a composition such as a pharmaceutical composition. Optionally the protective peptides described herein may be combined in a pharmaceutical composition or co-administered with an anticoagulant, thrombolytic agent, anti-inflammatory and/or cytoprotective agent.

The pharmaceutical compositions can be administered to humans or animals by a variety of methods including, but not restricted to topical administration, oral administration, aerosol administration, intratracheal instillation, intraperitoneal injection, injection into the cerebrospinal fluid, intravenous injection, intramuscular injection and subcutaneous injection. Dosages to be administered depend on patient needs, on the desired effect and on the chosen route of administration. Nucleic acid molecules and peptides may be introduced into cells using in vivo delivery vehicles such as liposomes. They may also be introduced into these cells using physical techniques such as microinjection and electroporation or chemical methods such as co-precipitation, pegylation or using liposomes.

The pharmaceutical compositions can be prepared by known methods for the preparation of pharmaceutically acceptable compositions which can be administered to patients. In an embodiment, an effective quantity of the nucleic acid molecule or peptide is combined in a mixture with a pharmaceutically acceptable carrier. Suitable carriers are described, for example in Remington's Pharmaceutical Sciences (Remington's Pharmaceutical Sciences, Mack Publishing Company, Easton, Pa., USA) or Handbook of Pharmaceutical Additives (compiled by Michael and Irene Ash, Gower Publishing Limited, Aldershot, England (1995). On this basis, the compositions include, albeit not exclusively, solutions of the substances in association with one or more pharmaceutically acceptable carriers or diluents, and may be contained in buffered solutions with a suitable pH and/or be iso-osmotic with physiological fluids.

On this basis, the pharmaceutical compositions provided herein optionally include an active compound or substance, such as a protective peptide, in association with one or more pharmaceutically acceptable carriers, such as a vehicle or diluent, and contained in buffered solutions with a suitable pH and iso-osmotic with the physiological fluids. The methods of combining the active molecules with the vehicles or combining them with diluents are well known to those skilled in the art. The composition optionally includes a targeting agent for the transport of the active compound to specified sites within tissue, such as to cardiac tissue or across the blood brain barrier.

Methods and Uses of C-Terminal GLP-1 Peptides for the Treatment or Prevention of Ischemic Tissue Injury In one aspect of the disclosure, there is provided a method for the treatment or prevention of ischemic tissue injury. In one embodiment, the methods involve administering to a subject in need thereof a protective peptide or composition comprising a protective peptide as described herein. In one aspect of the disclosure, there is also provided the use of a peptide or composition as described herein for the treatment or prevention of ischemic tissue injury in a subject in need thereof.

The administration or use of a protective peptide or composition for the treatment or prevention or ischemic tissue injury can be in vivo and/or ex vivo. In an embodiment, the amount of the peptide or composition used or administered to a subject is a therapeutically active amount at dosages and for periods of time necessary to achieve the desired result, namely the treatment or prevention of ischemic tissue injury. For example, a therapeutically active amount of a substance may vary according to factors such as the disease state, age, sex, and weight of the individual, and the ability of the substance to elicit a desired response in the individual. Dosage regimes may be adjusted to provide the optimum therapeutic or prophylactic response. Optionally, the peptides described herein may be administered by recombinant expression of nucleic acids encoding for the peptide in the subject, such as by methods of gene therapy.

In one embodiment, the peptides described herein are used or administered to a subject as a prophylactic for the prevention of tissue injury prior to, or following, an ischemic event. For example, in one embodiment the peptides described herein are used or administered to a subject who presents with one or more symptoms of an ischemic event such as a heart attack or stroke. In some embodiments, the peptides described herein are used prophylactically in a subject who has an increased risk of suffering an ischemic tissue injury, such as in a subject who has previously suffered a stroke or heart attack. In some embodiments, subjects with an increased risk of suffering an ischemic tissue injury include subjects with diabetes. In some embodiments, the peptides, methods and uses described herein are for the treatment or prevention of ischemic tissue injury in subjects without diabetes or in subjects who do not present with the symptoms of diabetes.

In some embodiments, the peptides described herein are used or administered to a subject on a regular schedule. For example, in one embodiment, the peptides are used or administered to a subject every hour, every 2 hours, every 4 hours, every 8 hours, every 12 hours, or once a day. In one embodiment, the peptides are used or administered to a subject every day, every 2 days, every 3 days, every week, every 10 days, every 2 weeks, or every month. In one embodiment the peptide is used or administered to a subject in a dose or formulation sufficient to result in the desired clinical effect, i.e. for the treatment or prevention of ischemic tissue injury. In one embodiment, the peptides described herein are used or administered to a subject in a dose or formulation sufficient to result in a steady state plasma concentration of the peptide greater than 1 picomolar or from about 1 picomolar to about 10 nanomolar. In one embodiment, the peptide is used, formulated for use or administered to a subject in a dose or formulation sufficient to result in a steady state plasma concentration of the peptide from about 5 picomolar to about 5 nanomolar. In one embodiment, the peptide is used, formulated for use or administered to a subject in a dose or formulation sufficient to result in a steady state plasma concentration of the peptide of about 50 picomolar, greater than 50 picomolar, greater than 100 picomolar, greater than 500 picomolar or greater than 1000 picomolar. In one embodiment, the peptide is used, formulated for use or administered to a subject in a dose or formulation sufficient to result in a steady state plasma concentration of less than about 5 nanomolar, or less than about 10 nanomolar. In one embodiment, the peptide is used, formulated for use or administered to a subject in a dose or formulation sufficient to result in a steady state plasma concentration of between about 50 picomolar and about 10 nanomolar, or between about 100 picomolar and about 5 nanomolar.

Nucleic Acids

In an embodiment, there is also provided an isolated nucleic acid encoding a protective peptide as described herein, such as a nucleic acid encoding a C-terminal peptide of GLP-1 or a peptide comprising all or part of the amino acid sequence FIAWLVKGR (SEQ ID NO: 1) or FIAWLVKGRG (SEQ ID NO: 2).

The peptides of the invention may be prepared by chemical synthesis or by using recombinant DNA methods. Accordingly, the invention includes nucleic acid molecules having a sequence that encodes a peptide of the invention. These sequences are readily incorporated according to procedures known in the art into an appropriate expression vector that ensures good expression of the peptide. Expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" means that the nucleic acid is linked to regulatory sequences in a manner that allows expression of the nucleic acid.

EXAMPLES

The following examples illustrate embodiments of the invention and do not limit the scope of the invention.

Materials and Methods

Animals

C57Bl/6 mice were obtained from Jackson Laboratories and housed for at least 2 weeks before experimentation in accordance with Guidelines for the Care and Use of Laboratory Animals (National Institute of Health Publication, revised 1996, No. 86-23).

Reagents

C-terminal amidated peptides were synthesized by Bachem (Torrance, Calif.) and supplied in trifluoroacetate salt with >98% purity as confirmed by HPLC. Amino acid sequences of test peptides and scrambled version are listed in Table 1. Osmotic pumps (Model #1002) were from Alzet® (Cupertino, Calif.). KH7 and 2,5-dideoxyadenosine (Ddox) were a generous gift. All other reagents were from Sigma-Aldrich (Ontario, Canada).

TABLE 1

Amino acid sequences of synthetic peptides

| Peptide name | Amino acid sequence | SEQ ID NO |
|---|---|---|
| Exendin-4 | H-HGEGTFTSDLSKQMEEEAVR LFIEWLKNGGPSSGAPPPS-$NH_2$ | 3 |
| GLP-1(7-36)$NH_2$ | H-HAEGTFTSDVSSYLEGQAA KEFIAWLVKGR-$NH_2$ | 4 |
| GLP-1(9-36)$NH_2$ | H-EGTFTSDVSSYLEGQAAKE FIAWLVKGR-$NH_2$ | 5 |
| GLP-1(28-36)$NH_2$ | H-FIAWLVKGR-$NH_2$ | 1 |
| SCRAM(28-36)$NH_2$ | H-AGKFWRILV-$NH_2$ | 6 |

Drug Infusion and Coronary Artery Ligation

Male, 10-12 week old, C57Bl/6 mice were anesthesized with intraperitoneal (i.p) ketamine 100 mg/kg (MTC Pharmaceuticals, Cambridge, Ontario, Canada) and xylazine 10 mg/kg (Bayer Inc., Etobicoke, Ontario, Canada) and implanted subcutaneously with osmotic pumps filled and primed (as per manufacturer's protocol) with either vehicle (0.8% saline) or peptide with targeted delivery of 18.5 nmol/kg/min for GLP-1(28-36)$NH_2$ and SCRAM(28-36) $NH_2$ 22 and 3.5 nmol/kg/min for GLP-1(7-36)$NH_2$ and GLP-1(9-36)$NH_2$(Zhang et al. 2007; Perry et al. 2007; Parlevliet et al. 2010).

After 2 weeks of continuous peptide infusion, animals were re-anesthesized with i.p ketamine/xylazine and underwent permanent ligation of the proximal left anterior descending (LAD) coronary artery to generate an experimental myocardial infarction (MI), as previously described (Ohta et al. 2004), with the surgeon blinded to treatment groups. At day 4 post-MI, animals were sacrificed and hearts excised for measurement of infarct size (FIG. 1B). This timepoint allows accurate measurement of infarct area prior to onset of cardiac rupture events (Noyan-Ashraf et al. 2005)

Infarct Measurement

Freshly excised hearts were washed twice in cold PBS to remove excess blood, and cut into 2 mm sections perpendicular to the long axis. The sections were incubated at 37° C. in 2% 2,3,5-triphenyltetrazolium chloride (TTC) for 15 min, after which they were washed with PBS and fixed in 4% paraformaldehyde for 1 h before image acquisition using a digital scanner. Image J software (NIH, USA) was used to measure infarct area (TTC unstained white area) and total left ventricle (LV) area. Measurements were performed by two independent investigators blinded to treatment groups, and percent infarct size was calculated as the average of both measurements (infarct area/total LV area×100%).

Isolated Heart Preparations and I/R Protocols

Male, 10-12 week old, C57Bl/6 mice were anesthesized with i.p ketamine (100 mg/kg)/xylazine (10 mg/kg)/heparin (1000 IU/kg), and the heart excised quickly, cannulated through the aorta, and perfused retrogradely with Kreb's Heinslet buffer in a Langendorff apparatus as previously described (Ban et al. 2008). Isolated hearts exhibiting a heart rate <300 bpm during first 10 min of perfusion were excluded from the study. A small plastic balloon connected to a pressure transducer was inflated inside the LV to measure LV end systolic (LVESP) and end diastolic pressure (LVEDP) obtained from computer analysis (AcqKnowledge 3.7.1. Biopack System, Goleta, Calif.). LVEDP was maintained at 4-8 mm Hg throughout the experiment. After 20 min of equilibration to allow the balloon to adjust inside the LV, hearts were perfused with buffer for 20 min, followed by 20 min perfusion with peptide of interest (FIG. 1a). Global ischemia was then generated by clamping inflow to the heart for 30 min, after which reperfusion was reinstated for 40 min. In the untreated control group, hearts were perfused for a total of 40 min prior to ischemia. LV developed pressure (LVDP) was calculated by subtracting LVEDP from LVESP. Functional recovery of LV function was calculated as LVDP at the end of reperfusion as a percentage of LVDP prior to ischemia.

cAMP Assay

After 24 h serum-deprivation, cells were pre-treated with the phosphodiesterase inhibitor IBMX (250 uM) for 30 min, after which the peptide of interest and/or vehicle PBS was added to the media to a final concentration of 30 nM for GLP-1 peptides and Exendin-4, and 10 uM for Isoproterenol and Forskolin. After 10 min drug treatment, cells were lysed and total intracellular cAMP release was measured using an enzymatic immunoassay kit (Cayman Chemicals, Mich.) as per manufacturer's protocol.

Example 1

Cardioprotective Effects of the GLP-1(28-36) Peptide

GLP-1(28-36)$^{amide}$ Reduces Infarct Size in a Mouse Model of MI.

Figure 1:
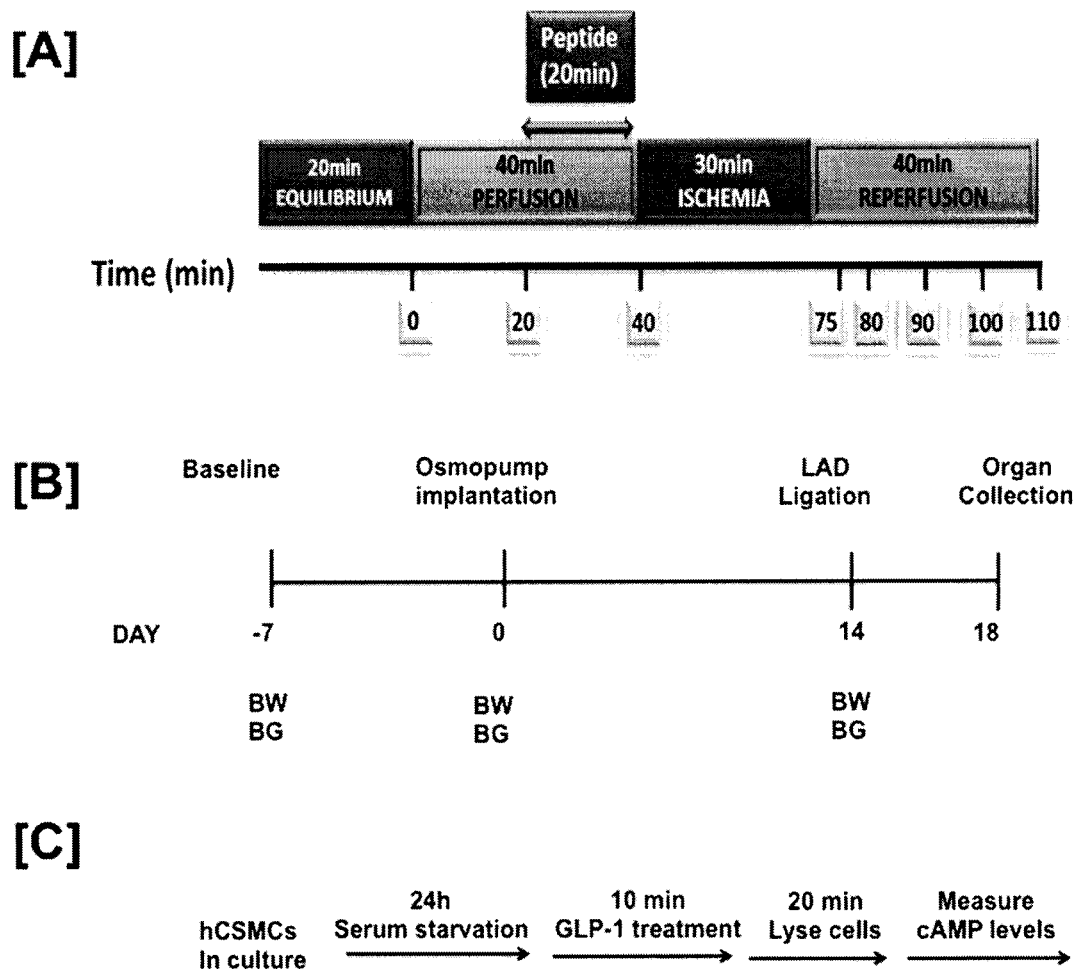
FIG. 1 shows experimental models used in the present disclosure. [A] Ex vivo Langendorff model of ischemia/reperfusion (I/R) injury in isolated wild-type (WT), 10-12 week old, male mouse hearts were used to characterize the pre-conditioning properties of GLP-1(28-36)$^{amide}$. Protocol showing sequence and duration of peptide infusions, ischemia, and reperfusion. [B] MI induced by ligation of left anterior descending artery in WT mice. Protocol showing 14-day duration of drug infusion, MI induction and organ collection. BW (Body weight); BG (Blood glucose). [C] Primary human coronary artery smooth muscle cells (hCSMCs) were treated with GLP-1(28-36)$^{amide}$ and cAMP release determined by an enzymatic immunoassay (Cayman Chemicals, MA).
Figure 2:
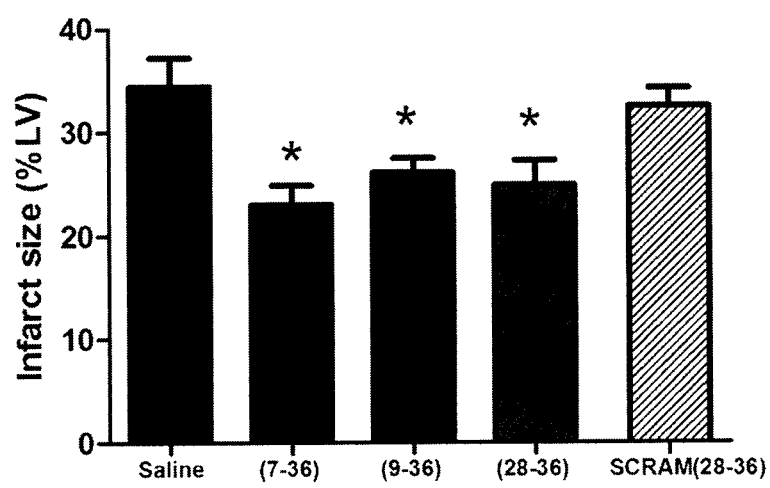
FIG. 2 shows that 14-day pre-infusion with GLP-1(28-36)$^{amide}$ in WT mice subjected to LAD ligation significantly reduced % LV infarct size after 4 days post-MI. Effect of no treatment (saline; n=8; 34.4±2.8%), GLP-1(7-36)$^{amide}$ (3.5 pmol/kg/min; n=13; 23.0±1.9%), GLP-1(9-36)$^{amide}$ (3.5 pmol/kg/min; n=7; 26.1±1.4%), GLP-1(28-36)$^{amide}$ (18.5 pmol/kg/min; n=7; 24.9±2.6%), SCRAM(28-36)$^{amide}$ (18.5 pmol/kg/min; n=7; 32.4±1.8%). All data are mean±SE. *P<0.05 vs saline control by one-way ANOVA.
Figure 2:

As shown in FIG. 1, an ex vivo Langendorff model of ischemia/reperfusion (I/R) injury in isolated wild-type (WT), 10-12 week old, male mouse hearts were used to characterize the preconditioning properties of the GLP-1 (28-36)$^{amide}$ peptide. Remarkably, infusion of the hearts with GLP-1(28-36)$^{amide}$ peptide prior to inducing ischemia by LAD ligation significantly reduced the size of the resulting left ventricle (LV) infarcts relative to treatment with a saline control or with a scrambled peptide (FIG. 2). More specifically, two-week pre-treatment with GLP-1 (28-36)$^{amide}$ (18.5 pmol/kg/min) significantly decreased LV infarct size at day 4 post-MI compared with SCRAM(28-36) and saline controls (24.9±2.4% n=7 vs. 34.4±2.8% n=7, P<0.05).

The observed cardioprotective effect of the GLP-1 j(28-36)$^{amide}$ peptide was comparable to that of the much longer GLP-1(7-36)$^{amide}$ (23.0%, n=13) which is known to activate the GLP-1 receptor and the GLP-1(9-36)$^{amide}$ peptide which may act through receptor-dependent and receptor-independent mechanisms.

Figure 3:
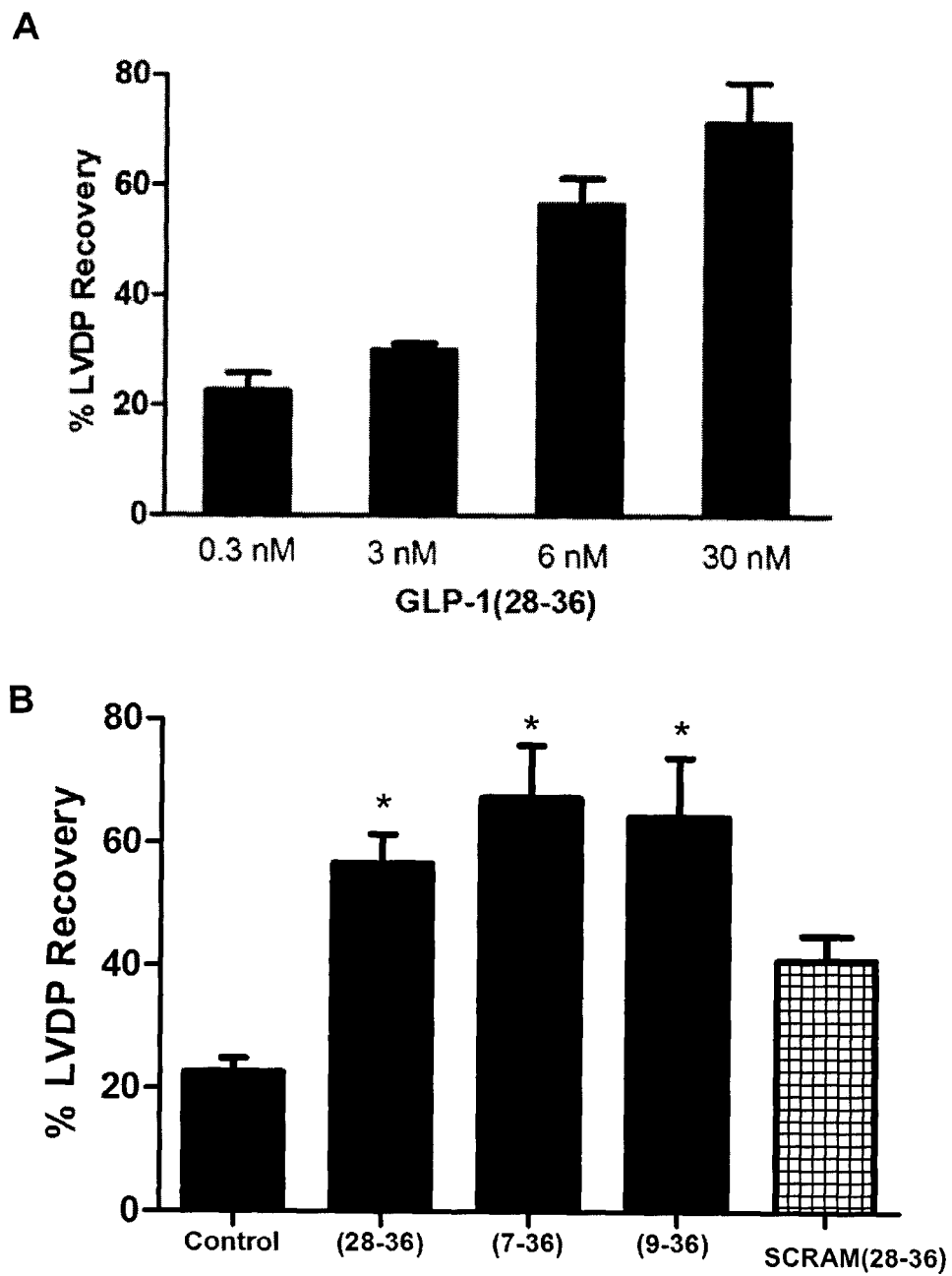
FIG. 3A shows the dose-dependent effect of GLP-1(28-36) on LVDP recovery in WT mice (n=4-12/group).
FIG. 3B shows functional recovery after I/R injury in WT mice pretreated with GLP-1 and the effect of no treatment and pretreatments with GLP-1 on LVDP in isolated WT hearts undergoing I/R injury. (control; n=13; 22.7±3.6%), GLP-1

Since both GLP-1(28-36)$^{amide}$ and it's parent GLP-1(7-36)$^{amide}$ have been previously shown to have body weight-dependent effects, body weights of the mice subjected to each treatment conditions at day 1 and day 14 of peptide infusion were compared. The data showed that both peptides did not significantly affect heart/body weight ratio or body weight after 14 days of infusion (FIG. 7A, 7B). Furthermore, since GLP-1(28-36) has previously demonstrated insulinotropic effects, and increased insulin secretion is known to cause preconditioning effects, non-fasting blood glucose levels were measured as an indicator of insulin release. There was non-significant change in blood glucose levels from day 1 to 14 in all treatment groups (FIG. 7C). These results strongly suggest that the reduction in infarct size in MI-induced mice is a direct effect of GLP-1(28-36)$^{amide}$ on the heart and not through any secondary organ mechanism. GLP-1(28-36)$^{amide}$ Exerts Cardiac-Specific Protective Actions, Independent of GLP1-Receptor The effect of the GLP-1(28-36)$^{amide}$ peptide on functional recovery was examined by measuring Left Ventriclular Developed Pressure (LVDP) post-reperfusion. A dose-dependent effect for GLP-1(28-36) on LVDP was observed, with minimum effective dose at 6 nM, a dose subsequently used in further experiments (FIG. 3A). As shown in FIG. 3B, pre-treatment with the GLP-1(28-36)$^{amide}$ peptide resulted in improved LVDP recovery compared to an untreated control. More specifically, recovery of LVDP was significantly greater in [28-36]$^{amide}$-vs. vehicle- or scrambled (28-36)-treated isolated hearts (57.6±6.6%, n=12 vs. 22.7±3.6%, n=13; P<0.05), and comparable to GLP-1(7-36) (67.3±8.6%, n=13) (FIG. 3B).

To further ascertain the protective actions of GLP-1(28-36)$^{amide}$, LDH release was measured in coronary effluents from the isolated perfused hearts as an indicator of cellular necrosis and death. As shown in FIG. 4, perfused hearts undergoing I/R injury released significant amounts of the cell death marker lactate dehydrogenase (LDH) in coronary effluents starting at around 75 minutes, reflecting cardiac cell injury and death due to ischemia. In contrast, a significantly lower concentration of LDH was observed in coronary effluent from hearts pretreated with the GLP-1(28-36)$^{amide}$ peptide. Pretreatment with the GLP-1(28-36)$^{amide}$ peptide therefore helps prevent cell death following an ischemic event and is useful for the treatment or prevention of ischemic tissue injury and ischemic heart disease.

Organs were collected on day 18 as shown in the experimental model set out in FIG. 1B and Western blots of heart lysates were processed. Western blots of hearts pre-treated with the GLP-1(28-36) peptide showed enhanced activation of Akt, Erk1/2, CREB and eNOS.

Next, it was investigated whether the cardioprotective actions of GLP-1(28-36)$^{amide}$ required the Gs-coupled GLP-1 receptor (GLP1R). The inventors previously demonstrated that the incretin hormone GLP-1(7-36)$^{amide}$ and its major metabolite, GLP-1(9-36)$^{amide}$, exhibited cardioprotective actions which were both dependent and independent of the GLP1R receptor (Ban et al. 2008; Ban et al. 2010). This observation unveils an additional cardioprotective pathway that does not depend on the putative Gs-coupled-adenylyl cyclase-cAMP-PKA mediated mechanism of action. To examine the cardioprotective mechanism of action of GLP-1(28-36)$^{amide}$, hearts isolated from GLP1R knockout mice (Glp1r-/-) were perfused undergoing I/R injury. Remarkably, Glp1r-/- hearts perfused with GLP-1 (28-36)$^{amide}$ demonstrated significantly higher recovery after I/R injury compared to saline or scrambled peptide controls and similar to GLP-1(7-36) (FIG. 8A). GLP-1(28-36)$^{amide}$ therefore exerts its cardioprotective actions independent of the GLP1R receptor. A schematic showing the proposed mechanism of action for cardioprotective peptides such as GLP-1(28-36) is shown in FIG. 8B.

GLP-1(28-36)$^{amide}$ does not Release cAMP from Cardiac Myocytes

To further explore the GLP1R-independent mechanism of action of GLP-1(28-36)$^{amide}$, studies were done to investigate whether GLP-1(28-36)$^{amide}$ could stimulate release of intracellular cAMP in vitro. cAMP is a crucial second messenger involved in the diverse pathways mediating the actions of incretin hormones. Using primary ventricular cardiomyoctyes isolated from neonatal WT mice, no cAMP response was detected from GLP-1(28-36)$^{amide}$ compared to PBS controls or scrambled peptide (FIG. 9A). Next, whether atrial cardiomyocytes could stimulate any cAMP response was tested. Using an mouse atrial cardiomyocyte cell line, HL-1 cells, no intracellular cAMP release with GLP-1(28-36)$^{amide}$ was observed, suggesting that the actions of GLP-1(28-36)$^{amide}$ was not localized to cardiomyocytes (FIG. 9B).

Example 2

Recovery after I/R Injury is Blocked by Soluble AC Inhibitors but not Transmembrane AC Inhibitors FIG. 5 presents data collected using the ex vivo mouse model of ischemia/reperfusion (I/R) injury for LVDP recovery in the presence or absence of the soluble adenylate cyclase (AC) inhibitor KH7 and the transmembrane AC inhibitor dideoxyadenosine. The protective effects of the GLP-1(28-36)$^{amide}$ peptide were blocked by the soluble AC inhibitor KH7, but not by the transmembrane AC inhibitor dideoxyadenosine (Ddox). More specifically, using isolated WT mice hearts perfused with the sAC inhibitor, KH7, we observed loss of cardioprotection with GLP-1(28-36)$^{amide}$ pre-treatment, but not with GLP-1(7-36)$^{amide}$ as measured by LVDP at the end of reperfusion (25.2±1.7 mmHg vs. 73.1±5.3 mmHg; P<0.0001) (FIG. 5). On the other hand, perfusing isolated hearts with DDox to inhibit tmAC, did not affect the cardioprotective actions of GLP-1(28-36)$^{amide}$ while the effect of GLP-1(7-36)$^{amide}$ was lost (67.6±5.8 mmHg vs. 27.1±5.3 mmHg; P<0.0001). The scrambled peptide SCRAM(28-36)$^{amide}$ did not produce any recovery of LV function in presence of either sAC inhibitor or tmAC inhibitor (36.4±5.2 mmHg vs. 37.6±5.3 mmHg respectively). Cardioprotection observed in GLP-1(28-36)$^{amide}$-perfused isolated mouse hearts undergoing I/R injury therefore appears to be dependent on sAC.

Example 3

Investigations of the GLP-1(28-36)$^{amide}$ Peptide Using hCSMCs

Tests performed in vitro using primary human coronary artery smooth muscle cells (hCSMCs) showed that GLP-1 (28-36)$^{amide}$ peptide caused dose-dependent increases in intracellular cAMP (FIG. 10). The source of cAMP in coronary smooth muscle cells was then investigated in view of unraveling a putative mechanism of action for GLP-1(28-36)$^{amide}$. Evidence is emerging of a second source of intracellular cAMP through the soluble adenylyl cyclase (sAC) enzyme, localized to cytosol, mitochondria or nucleus. As shown in FIG. 6, GLP-1(28-36)-mediated cAMP release in hCSMCs is soluble adenylate cyclase dependent and not dependent on transmembrane adenylate cyclase. In the presence of a specific inhibitor of sAC, KH7, the significant 2 fold increase in cAMP release mediated by GLP-1(28-36)

was abolished. However, inhibiting Gs-coupled transmembrane adenylyl cyclase (tmAC) with 2,5 didedoxyadenosine (Ddox), did not prevent the increase in cAMP generated by GLP-1(28-36)$^{amide}$. GLP-1(28-36)$^{amide}$ therefore mediates cAMP release through soluble adenylyl cyclase in coronary smooth muscle cells. Indeed, while sAC expression was abundantly detected in mouse heart lysates, western blot analysis showed that they were not expressed in either ventricular or atrial cardiac myocytes (FIG. 11A, B)

Example 4

Testing of C-Terminal GLP-1 Peptides as Neuroprotective Agents

The DPP-4 cleavage product of GLP-1, namely GLP-1(9-36)$^{amide}$, exhibits neuroprotective action in mice models of Alzheimer's disease, through the reduction of elevated levels of mitochondrial-derived reactive oxygen species as well as reversing the deactivation of the survival kinase GSK3β (See Ma et al. *Journal of Neuroscience* 2012:32(40); 13701-13708). However, the overall mechanism through which GLP-1(9-36)$^{amide}$ exerts neuroprotective effects is still unknown.

The C-terminal fragment GLP-1(28-36)$^{amide}$, derived from NEP cleavage of GLP-1(9-36)$^{amide}$, has also been shown to target to mitochondria and reduce oxidative stress (Tomas et al, 2011).

As shown in Example 1, GLP-1(28-36)$^{amide}$ protects tissue from cell death after ischemic injury in isolated mice hearts, as measured by decreased lactate dehydrogenase (LDH) release. Furthermore, as shown in Example 3 GLP-1(28-36)$^{amide}$ in vitro stimulates the release of cAMP, a second messenger involved in GSK3β activation. C-terminal domain GLP-1 peptides such as GLP-1(28-36)$^{amide}$ are therefore expected to display neuroprotective actions in conditions of brain ischemic injury, such as stroke. Shorter protective peptides, such as the nine-amino acid GLP-1(28-36)$^{amide}$, are also considered to be better candidates for drug development as neuroprotective agents, versus e.g. the longer 28-amino acid parent peptide which activate the GLP-1 receptor and may cause undesirable side effects.

Peptides corresponding to the C-terminal domain of GLP-1 as described herein including GLP-1(28-36)$^{amide}$ are tested in a mouse model of ischemic stroke. GLP-1(28-36)$^{amide}$ is infused via Alzet® osmotic mini pumps brain infusion kits, specialized for targeted infusion into cerebral ventricles. After 28 days of GLP-1(28-36)$^{amide}$ infusion, stroke is generated, after which brain infarct sizes are determined by TTC staining.

Protein lysates from brain tissue are extracted and the expression of survival kinases is probed by Western blots. Full length GLP-1(7-36)$^{amide}$ and GLP-1(9-36)$^{amide}$ are used as positive controls, while a scrambled peptide of GLP-1(28-36)$^{amide}$ is the negative control.

Treatment with peptides corresponding to the C-terminal domain of GLP-1 including GLP-1(28-36)$^{amide}$ are seen to result in smaller infarct sizes and upregulation of survival kinases.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Ban K, Noyan-Ashraf M H, Hoefer J, Bolz S S, Drucker D J, Husain M. Cardioprotective and vasodilatory actions of glucagon-like peptide 1 receptor are mediated through both glucagon-like peptide 1 receptor-dependent and -independent pathways. Circulation. 2008; 117:2340-2350

Ban K, Kim K H, Cho C K, Sauvé M, Diamandis E P, Backx P H, Drucker D J, Husain M. Glucagon-like peptide (GLP)-1(9-36)amide-mediated cytoprotection is blocked by exendin(9-39) yet does not require the known GLP-1 receptor. *Endocrinology*. 2010 April; 151(4): 1520-31.

Buse J B, Rosenstock J, Sesti G, Schmidt W E, Montanya E, Brett J H, Zychma M, Blonde L; LEAD-6 Study Group Liraglutide once a day versus exenatide twice a day for type 2 diabetes: a 26-week randomised, parallel-group, multinational, open-label trial (LEAD-6). *Lancet* 2009; 374(9683): 39-47.

Diamant M, Van Gaal L, Stranks S, Northrup J, Cao D, Taylor K, Trautmann M. Once weekly exenatide compared with insulin glargine titrated to target in patients with type 2 diabetes (DURATION-3): an open-label randomised trial. *Lancet* 2010; 375(9733): 2234-2243

Griffioen K J, Wan R, Okun E, Wang X, Lovett-Barr M R, Li Y, Mughal M R, Mendelowitz D, Mattson M P. GLP-1 receptor stimulation depresses heart rate variability and inhibits neurotransmission to cardiac vagal neurons. *Cardiovasc Res* 2011; 89: 72-78

Ma T, Du X, Pick J E, Sui G, Brownlee M, Klann E. Glucagon-like peptide-1 cleavage product GLP-1(9-36) amide rescues synaptic plasticity and memory deficits in Alzheimer's disease model mice. *Journal of Neuroscience* 2012:32(40); 13701-13708

Noyan-Ashraf M H, Momen M A, Ban K, Sadi A M, Zhou Y Q, Riazi A M, Baggio L L, Henkelman R M, Husain M, Drucker D J. Glp-1r agonist liraglutide activates cytoprotective pathways and improves outcomes after experimental myocardial infarction in mice. *Diabetes*. 2009; 58:975-983

Ohta K, Nakajima T, Cheah A Y, Zaidi S H, Kaviani N, Dawood F, You X M, Liu P, Husain M, Rabinovitch M. Elafin-overexpressing mice have improved cardiac function after myocardial infarction. *American journal of physiology. Heart and circulatory physiology*. 2004; 287: H286-292

Parlevliet E T, de Leeuw van Weenen J E, Romijn J A, Piji H. Glp-1 treatment reduces endogenous insulin resistance via activation of central glp-1 receptors in mice fed a high-fat diet. *American journal of physiology. Endocrinology and metabolism*. 2010; 299:E318-324

Perry T, Holloway H W, Weerasuriya A, Mouton P R, Duffy K, Mattison J A, Greig N H. Evidence of glp-1-mediated neuroprotection in an animal model of pyridoxine-induced peripheral sensory neuropathy. *Experimental neurology*. 2007; 203:293-301

Read P A, Hoole S P, White P A, Khan F Z, O'Sullivan M, West N E, Dutka D P. A pilot study to assess whether glucagon-like peptide-1 protects the heart from ischemic dysfunction and attenuates stunning after coronary balloon occlusion in humans. *Circulation. Cardiovascular interventions*. 2011; 4:266-272

Tomas E, Stanojevic V, Habener J F. GLP-1-derived nonapeptide GLP-1(28-36)amide targets to mitochondria and suppresses glucose production and oxidative stress in isolated mouse hepatocytes. *Regul Pept*. 2011 Apr. 11; 167(2-3):177-84

Zhang J, Tokui Y, Yamagata K, Kozawa J, Sayama K, Iwahashi H, Okita K, Miuchi M, Konya H, Hamaguchi T, Namba M, Shimomura I, Miyagawa W. Continuous stimulation of human glucagon-like peptide-1 (7-36) amide in a mouse model (nod) delays onset of autoimmune type 1 diabetes. *Diabetologia*. 2007; 50:1900-1909

We claim:

1. A method for the treatment of cardiac ischemic tissue injury or reducing cardiac ischemic tissue injury or improving functional recovery of the heart following an ischemic event comprising administering to a subject in need thereof an effective amount of a peptide consisting of the amino acid sequence FIAWLVKGR (SEQ ID NO: 1) or FIAWLVKGRG (SEQ ID NO: 2) for the treatment of cardiac ischemic tissue injury or reducing cardiac ischemic tissue injury or improving functional recovery of the heart following the ischemic event in the subject.

2. The method of claim 1, wherein the peptide consists of the amino acid sequence FIAWLVKGR (SEQ ID NO: 1).

3. The method of claim 1, wherein the peptide consists of the amino acid sequence FIAWLVKGRG (SEQ ID NO: 2).

4. The method of claim 1, wherein the C-terminus of the peptide is amidated.

5. The method of claim 1, wherein the effective amount of the peptide is protective against cardiac ischemia/reperfusion injury, ischemia-induced cardiac cell death or myocardial infarction.

6. The method of claim 1, wherein the effective amount of the peptide is cardioprotective against ischemic-induced loss of left ventricle developed pressure (LVDP).

7. The method of claim 1, wherein the effective amount of the peptide induces an increase in intracellular levels of cyclic adenosine monophosphate (cAMP) in cardiac muscle cells or smooth muscle cells.

8. The method of claim 7, wherein the increase in intracellular levels of cAMP is dependent on soluble adenylate cyclase.

9. The method of claim 1, for the treatment of ischemic tissue injury caused by ischemic heart disease.

10. The method of claim 9, further comprising identifying the subject as having an increased risk of ischemic heart disease relative to a normal population prior to administering the peptide.

11. The method of claim 1, further comprising the step of identifying the subject as having previously had a myocardial infarction prior to administering the peptide.

12. The method of claim 1, wherein the subject has an increased risk of cardiotoxicity.

13. The method of claim 1, wherein the peptide is administered as a prophylactic for the prevention of cardiac ischemic tissue injury following the ischemic event.

14. The method of claim 1, comprising administering to the subject a dose sufficient to result in a steady state plasma concentration of the peptide from about 1 picomolar to about 10 nanomolar.

15. The method of claim 1, wherein the subject is a human.

16. The method of claim 1, wherein the peptide is administered to the subject in a composition comprising a pharmaceutically acceptable carrier.

17. The method of claim 1, wherein the peptide is administered to the subject within 2 weeks of the ischemic event.

18. The method of claim 1, wherein the subject has not been diagnosed with diabetes.

19. The method of claim 13, wherein the ischemic event is a myocardial infarction.

* * * * *

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Human peptide fragments

<400> SEQUENCE: 1

Phe Ile Ala Trp Leu Val Lys Gly Arg
1               5

<210> SEQ ID NO 2
<211> LENGTH: 10
<212> TYPE: PRT
<213> ORGANISM: Artificial Sequence
<220> FEATURE:
<223> OTHER INFORMATION: Human peptide fragments

<400> SEQUENCE: 2

Phe Ile Ala Trp Leu Val Lys Gly Arg Gly
1               5                   10

<210> SEQ ID NO 3
<211> LENGTH: 39
<212> TYPE: PRT
<213> ORGANISM: Artificial Sequence
<220> FEATURE:
<223> OTHER INFORMATION: Synthetic peptide

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 30
<212> TYPE: PRT
<213> ORGANISM: Artificial Sequence
<220> FEATURE:
<223> OTHER INFORMATION: Human peptide fragment

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 28
<212> TYPE: PRT
<213> ORGANISM: Artificial Sequence
<220> FEATURE:
<223> OTHER INFORMATION: Human peptide fragments

<400> SEQUENCE: 5

Glu Gly Thr Phe Thr Ser Asp Val Ser Ser Tyr Leu Glu Gly Gln Ala
```

```
1               5                   10                  15
Ala Lys Glu Phe Ile Ala Trp Leu Val Lys Gly Arg
                20                  25

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Ala Gly Lys Phe Trp Arg Ile Leu Val
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide

<400> SEQUENCE: 7

Gly Gly Gly Tyr Gly Arg Lys Lys Arg Arg Gln Arg Arg Arg
1               5                   10
```